United States Patent [19]

Sutherland et al.

[11] Patent Number: 4,775,637

[45] Date of Patent: Oct. 4, 1988

[54] AN IMMUNOASSAY APPARATUS HAVING AT LEAST TWO WAVEGUIDES AND METHOD FOR ITS USE

[75] Inventors: Ranald M. Sutherland, Geneva; Claus Dähne; Georges Revillet, both of Onex, all of Switzerland

[73] Assignee: Purtec Limited, London, England

[21] Appl. No.: 804,845

[22] Filed: Dec. 5, 1985

[30] Foreign Application Priority Data

Dec. 10, 1984 [EP] European Pat. Off. .......... 8481601.9

[51] Int. Cl.[4] .................. G01N 21/00; G01N 33/552; G01N 33/72

[52] U.S. Cl. ..................................... 436/527; 250/227; 250/302; 250/365; 356/445; 422/57; 422/68; 436/67; 436/165; 436/172; 436/805

[58] Field of Search ............... 250/227, 302, 365; 356/445; 436/165, 172, 805, 67; 422/57, 68

[56] References Cited

U.S. PATENT DOCUMENTS

| | | |
|---|---|---|
| 4,399,099 | 8/1983 | Buckles .......................... 436/805 X |
| 4,451,434 | 5/1984 | Hart ................................ 436/805 X |
| 4,558,014 | 12/1985 | Hirschfeld et al. . |
| 4,582,809 | 4/1986 | Block ............................. 436/805 X |
| 4,654,532 | 3/1987 | Hirschfeld . |
| 4,671,938 | 6/1987 | Cook . |

*Primary Examiner*—Sidney Marantz
*Attorney, Agent, or Firm*—Cushman, Darby & Cushman

[57] ABSTRACT

The unit consists of a cuvette and light guiding means comporting more than one waveguide element in contact with the solution to be analyzed. During operation, signals issuing from said waveguide elements provide data on two or more parameters in the solution substantially simultaneously.

8 Claims, 3 Drawing Sheets

AN IMMUNOASSAY APPARATUS HAVING AT LEAST TWO WAVEGUIDES AND METHOD FOR ITS USE

The present invention concerns a combination unit or assembly including an analytical cuvette and light guiding means usable in an apparatus for optically determining species in solution, more especially for determining bioactive species by reactions of the immunoassay type.

Analytical apparatuses comprising optical fiber probes which can optically monitor the adsorption of chemical species on the fiber core are known. This technique is based on the immersion of an illuminated optical waveguide, for instance an optical fiber the cladding of which is removed in a test solution the refractive index of which is lower than that of the fiber core, whereby an interaction takes place between the evanescent wave component of the light signal travelling along the waveguide and some species in solution to be determined. This approach is particularly interesting for monitoring events in the reaction space in close vicinity to the fiber, i.e. within reach of the evanescent wave component (a few tens or hundreds of nanometers), this being in the case of tests based on the reaction of a first partner in a complexation reaction, this partner being adsorbed or attached on the probe surface, with a second partner dissolved in the sample solution.

Apparatuses suitable for such types of measurements have been recently disclosed in the following references WO No. 84/00817; U.S. Pat. No. 4,447,546 (HIRSCHFELD et al); GB No. 2,103,786 (ICI); J. D. ANDRADE et al. Applied optics 23 (11) 1984, 1812–1815; WO-A-8100912 (BUCKLES); U.S. Pat. No. 4,050,895 (HARDY et al); U.S. Pat. No. 3,939,350 (KRONICK et al).

Recently, there has been disclosed (see EP-A-75353) an apparatus for measuring parameters in a reaction of an analyte with a specific reactant thereto, said reaction occurring on the surface of a waveguide, e.g. a piece of optical fiber core, and causing detectable changes to the optical properties thereof, which comprises a light source, means to inject a signal from that source into the input of said waveguide, detecting means to detect the light signal having undergone changes when travelling therethrough and emerging therefrom and converting it to an electric signal, and means for processing said signal into useful data pertaining to said reaction. This apparatus comprises:

(a) A waveguide, the main part of which passes through a container or cuvette for holding a liquid analyte to be determined; the exposed surface of the waveguide immersed in the liquid is coated, before operation, with a thin film of a specific complexing reagent of the species dissolved in the liquid and which should be determined. The assembly of the waveguide and the cuvette constitutes the test probe of the apparatus.

(b) A light source, a collimating lens, an annular aperture and a focusing lens for injecting into the waveguide a light beam originating from the source and directed by the focusing lens at a selected angle to ensure propagation of the beam by multiple reflections in the probe fiber.

(c) The disclosed apparatus further comprises a main detector for transforming the exit light signal from the output end of the core into an electric signal, amplifying and computing circuits to process the signal from the detector and, finally, a display device providing the desired read-out output.

Although the previously disclosed waveguide probe and cuvette assembly for performing the chemical reaction to be monitored have been operated satisfactorily in the past, it was found desirable to provide other systems which can be set-up faster, are easier to operate and which can provide information, more or less simultaneously, on more than one parameter of the analytical solution.

The present combination assembly, as defined in claim 1 is an accomplishment of the afore-mentioned wishes. One embodiment of this assembly with an apparatus in which it is incorporated as well as modifications thereof will now be described with reference to the annexed drawing.

Figure 1:
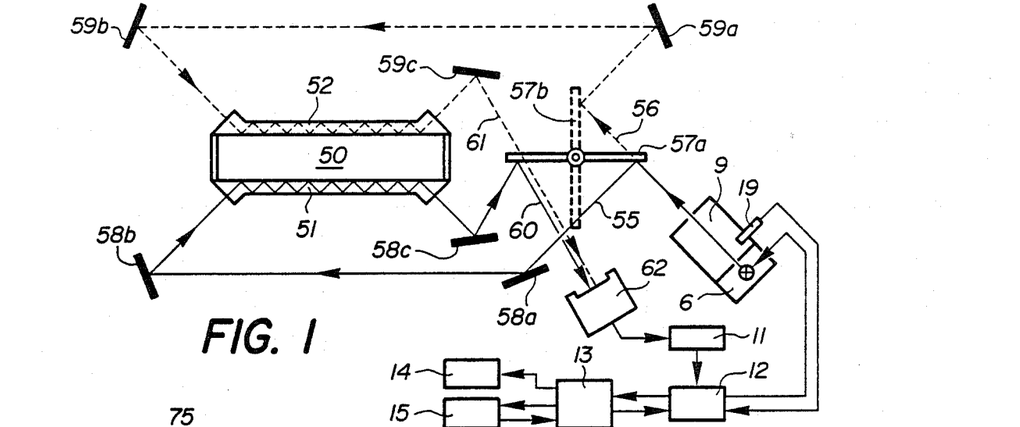
FIG. 1 is a schematic top view of an embodiment of an analytical apparatus involving a double waveguide cell combination assembly.

The apparatus of which the essential optical components are schematized on FIG. 1 comprises a dual-element waveguide cell 50 of which the main walls 51 and 52 constituting the two light guiding elements carry exciting signals originating from a source 6. The inner walls of this cuvette are in contact with the analyte solution contained in cell 50. The especially shaped light conductive walls of the cuvette can be provided by usual means, e.g. by molding of a transparent plastic, for instance lucite or they can be made of glass, preferably optical grade. The width of the cuvette, i.e. the distance between walls 51 and 52 is any, compatible with the holding of an amount of analyte sufficient for analysis; this width can be a few mm or a fraction of a mm (e.g. 10 to 1000 um) in which case the cuvette can also act as a sampling means due to the capillary effect provided by walls arranged very near to each other.

A beam of light originating from a source 6 is alternatively split into beams 55 and 56 by a rotating chopper mirror 57a, b. On FIG. 1, this mirror 57 has been represented in two positions, i.e. one position corresponds to numeral 57a and another position (at about right angle to the first one) by numeral 57b. It can be readily seen that, depending upon the position of the mirror 57, the original beam is either reflected into beam 55 or propagated into beam 56. Thus, the light from the source 6 is alternatively injected in either portion 51 or 52 of the dual waveguide cell 50 by means of either one of a series of mirror 58a, b, c and 59a, b and c, respectively. The output light, respectively by reflection at the chopper blade 60 and directly 61, from either part of the waveguide is then collected on a detector 62.

The remaining components of this embodiment comprise a monochromator 9 and electronic elements with data-acquisition and processing microcomputer including a photodetector 62, a preamplifier 11, a light source with intensity control system 12, a microprocessor 13, a printer 14, and a memory (floppy disc) 15.

The light source 6 used preferably was a xenon flash lamp (E. G. & G., Salem, MA) and the monochromator was preferably equipped with a concave holographic grating (Jobin-Yvon, Paris, France) to permit a resolution of 5 mm. The flash lamp of the source 6 was controlled by the microcomputer 12. To inject the samples to the cell 50 a programmable automatic pipette (Microlab-P; Hamilton Bonaduz AG, Bonaduz, Switzerland) was used preferably. The detector 62 comprised a photomultiplier tube (R928; Hamamatsu, Tokyo, Japan) placed at the waveguide output to monitor the change in light intensity directly. Signals from the photoamplifier tube were amplified (11), integrated during the flash time (12) and converted by a standard 12-bit analog/digital converter (not shown) into digital format. The in-house developed miicrocomputer 12 performed fast signal averaging, and all data were adjusted for variation in flash lamp intensity by reference to a photodiode 19 placed in the monochromator. The signals were transmitted to an Apple II microcomputer 13 for display and storage.

In a further embodiment, (see FIG. 2), the apparatus comprises a dual-waveguide cell 70 identical with the cell of the previous embodiment, i.e. having walls 71 and 72 acting as the two independent elements of the waveguide and operating similarly as will be seen.

Figure 2:
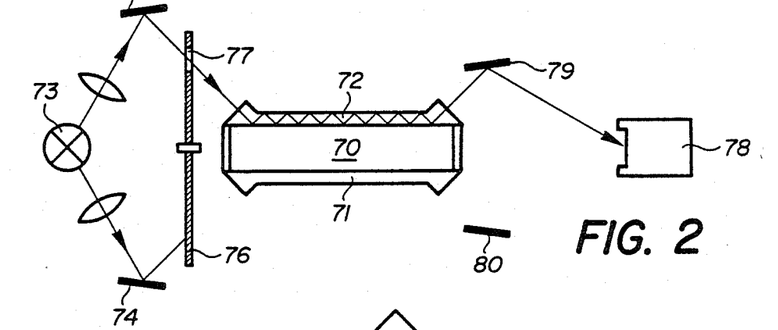
FIG. 2 is a schematic view of a variant of the embodiment of FIG. 1.

The apparatus comprises a light source 73, the output of which is focused on either side by means of lenses and mirrors on the input side of guide elements 71 and 72. The mirrors have numerals 74 and 75. A chopper disc 76 with a window hole 77 acts to alternatively distribute the incident light into elements 71 and 72. The output signals from the waveguide are then directed to a detector 78 by means of mirrors 79 and 80.

In both embodiments depicted on FIGS. 1 and 2, one of the waveguide elements (51, 71) is coated with a specific binding species e.g. an antibody specific to one component to be measured in the analyte by a complexation reaction (as disclosed hereintofore) while the second element (52, 72) is left uncoated. Herein, uncoated refers to a surface without antibody. However the protein adsorption sites on this surface are usually blocked by adsorbing an alternative non reactive or non-binding protein (e.g. bovine serum albumin BSA) to the surface. Therefore during analysis, the signal at the output of the uncoated area reflects the interaction of the exciting beam with the bulk of the analyte. However, (alternately, simultaneously or nearly simultaneously) the signal emerging from the coated side of the guide provides the required information on the component being bound by the specific reactant coated on the inner surface of this side of the cell. This will be illustrated in more detail with reference to the examples in this application. Suffice to say now that this kind of waveguide system (dual type) allows to gather the two types of information from separate elements of the waveguide. Evidently, the detector output signal in this embodiment is thereafter processed and converted into readout data as disclosed in connection with the previous embodiment. As a modification, the waveguide elements 51, 52 or 71, 72 can be coated with different antibodies each specific to one particular species in the analyte; in this modification the analytical results then relate to said two species being bound by said antibodies on each separate element of the waveguide.

Figure 3:
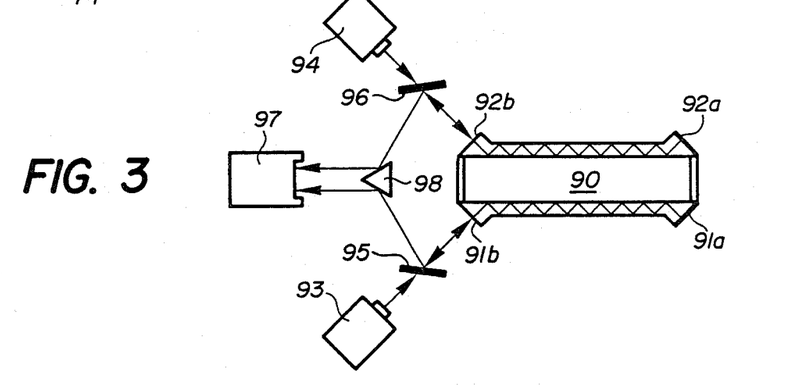
FIG. 3 is a schematic view of still another embodiment.

Another variant embodiment is represented on FIG. 3. In this variant, a dual waveguide cell 90 of the same general configuration as the aforementioned cells 50 and 70 is used with the difference that ends 91a and 92a are actually made reflective, for instance by metallizing (silver or aluminum) like in the case of a mirror. Therefore, the other ends 91b and 92b, respectively, of the waveguide light conductive elements act simultaneously as the input and output ends. This is illustrated by the paths of the exciting light beams provided by two sources 93 and 94 which are directed into ends 91b and 92b, respectively, after crossing beam-splitters 95 and 96, respectively. Thus, the light which penetrates through ends 91b and 92b travels through the guide first in a forward direction and then backwards after being reflected from ends 91a and 92a. This configuration enables that the interaction capacity of the exciting light with the analytes be actually doubled as compared with the previously disclosed embodiments. This variant further comprises a detector 97 for collecting the backward signals exiting from 91b and 92b and directed thereto by means of beam splitters 95 and 96 and a triangular-chaped mirror 98. Sources 93 and 94, e.g. LEDS, are alternatingly synchronized by means known in the art so that signal pulses exiting from the waveguide ends 91b and 92b do not simultaneously fall on the detector 97. Naturally, other types of cuvette-waveguide units with more than two waveguides elements are also possible, for instance cuvettes containing optical fiber waveguides in addition of the opposite facing walls thereof working as waveguides. Therefore the total number of independent waveguides elements operating together in the unit being larger than 2, a corresponding number of parameters of the solution can be investigated simultaneously (or about simultaneously).

The use of the afore-disclosed apparatuses can be illustrated by the analysis of blood samples as provided hereinafter.

Indeed, the direct determinations in blood samples of hemoglobin and various other hemoglobin factors such as glycosylated hemoglobin, this being, if desired, relative to total hemoglobin in this sample constitute very important medical tests. It is known that glycosylated hemoglobins ($HbA_{1a}$, $A_{1b}$ and $A_{1c}$) are important factors in the diagnosis and monitoring of patients with diabetes. The determination of the content of $HbA_{1c}$ (which amounts to about 80% of total glycosylated hemoglobins ($HbA_1$)) relative to total hemoglobin (i.e. $HbA_o$, non-glycosylated hemoglobin and $HbA_1$) is particularly important with regard to that disease.

Hemoglobin $A_{1c}$ is a glycohemoglobin with an amino acid structure which is identical to that of $HbA_o$; the important difference is the presence of 1-amino-1-deoxy-fructose attached in the 2,3-di-phosphoglycerate pocket to the N-terminal valine in the beta-chain of $HbA_{1c}$. The modification of $HbA_o$ to $HbA_{1c}$ is a continuous non-emzymatic post-translational process, the rate of which is a function of the blood glucose concentration. Glycosylation occurs as a two step process. Firstly, the open aldehydic form of glucose reacts with the terminal amino group of the beta-chains of Hb to form a SCHIFF base. Secondly, the SCHIFF base then undergoes an AMADORI rearrangement to form $HbA_{1c}$. The intermediate SCHIFF base is unstable with a 60-fold greater tendency to dissociate (to the free sugar plus protein) than the stable ketoamine of $HbA_{1c}$. As only a small fraction of blood glucose is in the open aldehydic form (approximately 10-6%) and the rate of ketoamine formation is slow (although effectively irreversible), the formation of $HbA_{1c}$ is an indication of long term blood glucose concentration. Over the 120 days life-span of the human red blood cell, the number of glycosylated Hb molecules increases proportionally to the mean blood glucose concentration. The relationship between the mean plasma glucose and $HbA_{1c}$ concentration is unique in that a single $HbA_{1c}$ extinction measurement provides a retrospective assessment of blood glucose control over the preceeding 6 to 8 weeks. It is generally accepted that $HbA_{1c}$ measurements are a very useful tool in monitoring diseases of carbohydrate metabolims, specifically diabetes mellitus. Diabetics have high long-term blood sugar levels and this is reflected in their $HbA_{1c}$ levels. Normal adults have about 3-6% of their total hemoglobin as $HbA_{1c}$ whereas the range in juvenile and maturity onset diabetics is 6-15% as $HbA_{1c}$. A similar increase in $HbA_{1c}$ concentration has been noted in mice with genetic and chemically induced diabetes and in pancreatectomized dogs.

Among the several methods which exist for determining glycosylated Hb in blood, $HbA_1$ and in particular $HbA_{1c}$ measurements have now become a method of choice for monitoring the treatment of diabetics (L. JOVANOVIC et al., American J. of Medicine (1981) 70, 331; D. E. GOLDSTEIN et al., Diabetes (1982) 31, 70; K. H. GABBOY et al., J. of Clinical Endocrinology and Metabolism (1977) 44, 859; B. GONEN et al., Diabetologia (1978) 15, 1; C. M. PETERSON, Diabetes (1982) 31, 1). Also, the following patent documents can be usefully mentioned: U.S. Pat. No. 4,247,553; GB-A-1,580,318; U.S. Pat. No. 4,222,836; U.S. Pat. No. 4,372,747; U.S. Pat. No. 4,200,435; U.S. Pat. No. 4,341,635. These methods can be readily classified by the mechanism used to separate glycosylated Hb from non-glycosylated Hb. For instance ion-exchange chromatography was used early and is still the most common method (H. G. KUNKEL et al., Science (1955) 122, 288). Although such ion-exchange technique is currently the only available method which specifically measures $HbA_{1c}$, it has a number of limitations of which temperature and pH sensitivity are the most important. Ion-exchange also is subject to interferences as labile glycosylated Hb (pre-$HbA_{1c}$) must be removed prior to assay and both fetal Hb (HbF) and Sickle Cell Hb (HbS) interfere with the results.

Other techniques involve agar gel electrophoresis (L. MENARD et al., Clinical Chemistry (1980) 26, 1598), isoelectric focusing (K. M. SPICER et al., Diabetes (1978) 27, 384), colorimetry, e.g. with thiobarbituric acid (R. FLUCKIGER et al., FEBS Letters (1976) 71, 356) and affinity chromatography (V. BOURIOTIS et al., Diabetologia (1981) 21, 579). Only one type radioimmunoassay has been reported (J. JAVID et al., British J. of Haematology (1978) 38, 329) which was slow (more than 3 days to work) and technically complex as requiring the preparations of radiolabelled $HbA_{1c}$. Although the methods of the prior art have merits, there is still a need for methods providing quick results (less than about 15 minutes), requiring less skilled operators and less costly to be undertaken on a routine basis. Current art methods are slow (typically results after more than 1 hour) technically complicated (require more than five pipetting manipulation steps) and unsuited to testing outside a laboratory environment. Further, present methods require that total hemoglobin be ascertained separately from the glycosylated factors and it was desirable that both analytical data could be ascertained substantially together and correlated without delay.

The method which can be performed with the apparatus disclosed in the present invention remedies the inconvenience of prior art methods and enables to determine about simultaneously more than one parameter in the blood; it further offers the advantage of directly providing, if desired, the percent of one parameter, e.g. glycosylated factor or other hemoglobin factors relative to another parameter, e.g. total hemoglobin.

This illustrative method allows for the separate determination of Hb-$A_{1c}$, $A_{1a}$ or $A_{1b}$ provided antibodies specific to any of such species are available in purified form. Otherwise, using less specific antibodies, the present method allows for the combined determination of two or more blood factors taken together, i.e. all glycosylated Hb relative to total Hb for instance. Of course, the method also provides for the determination of blood factors other than the ones hereabove if corresponding reagents specific to said factors in complex formation reactions are available (e.g. HbF, HbS or other human hemoglobin variants).

The method does not concern the obtention or preparation of such specifically reactive complex moieties (monoclonal or polyclonal antibodies) but it concerns their use as coating materials in the preparation of the active waveguides to be contacted with the blood sample to be analyzed with the assembly of the invention.

The optical technique used here relates, as heretofore mentioned, mainly to light absorption, i.e. there is an interaction of the evanescent component of the wave transported in one operative element of the guide with the molecules, first in the ambient liquid and, second, with the Hb-antibody complex which starts building up on the guide in form of a layer due to the reaction of the blood factor to be determined with the specific complex moiety (antibody) previously coated on the surface of another operatively distinct element of the waveguide. The depth of interaction of the evanescent light component in the corresponding element is substantially limited to the thickness of the layer of the complex so the optical response to that build-up is independent of the bulk adsorption due to the blood itself and the two effects can be easily distinguished with relatively simple techniques for decoding the signals originating from one or the other effect.

Hb derivatives have characteristic adsorption spectra dependent on their chemical state. Hence, any of the usual adsorptiometric techniques are equally applicable for implementing the invention (L. TENTORI et al., Hemoglobin, in Methods in Enzymology (1981), vol. 76, 707-732, Academic Press, New-York). Included are the cyanomethemoglobin method and single or multi-wavelength absorptio-metric assays, preferably in the range 400 to 600 nm, specifically 400-420 nm and 550-600 nm. Also included are such isobestic point methods where the absorption by the Hb molecule is independent of the degree of oxygen saturation.

Figure 4:
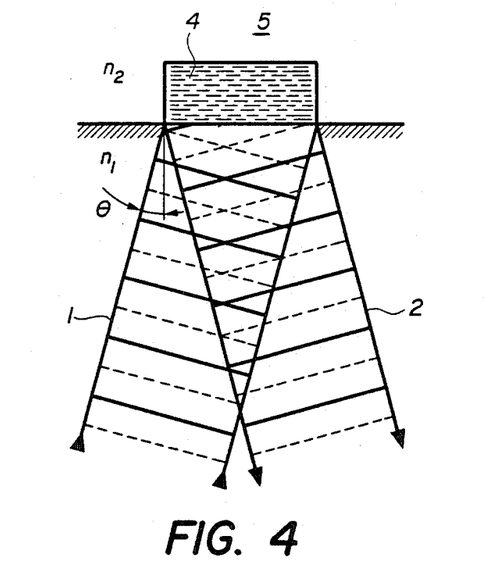
FIG. 4 is a diagram explaining the propagation of totally reflected light in a medium (waveguide) of refractive index $n_1$ greater than $n_2$, the refractive index of another medium (analyte) with which the waveguide is in contact.

The operation of the present test proceeds according to the following: when a light beam 1 strikes with an angle $\theta$ the interface between two transparent media $n_1$ and $n_2$ (FIG. 4) striking from the medium $n_1$ with the greater refractive index ($n_1 > n_2$), total internal reflection occurs (N. J. HARRICK, Internal Reflexion Spectroscopy, Wiley Interscience, New-York (1967)) when the angle of reflection $\sigma$ is larger than a certain value $\theta_c$ called the critical angle given by the equation:

$$\theta_c = \sin^{-1}(n_2/n_1) \qquad 1$$

Figure 5:
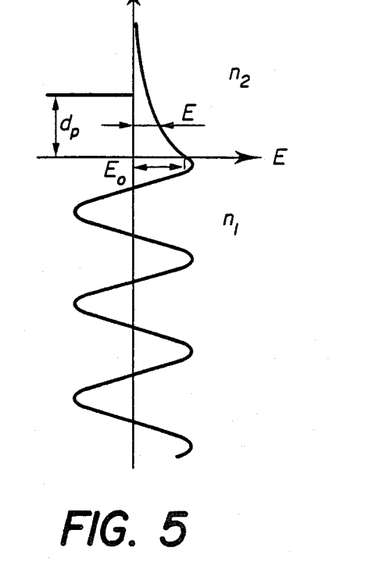
FIG. 5 is appendent to FIG. 4 and schematically represents the penetration of the evanescent wave component in the rarer medium (analyte).

The reflected beam is indicated by numeral 2. In this case the evanescent wave penetrates a distance ($d_p$) of the order of a fraction of a wavelength beyond the reflecting surface into the rarer medium of refractive index $n_2$. According to Maxwell's equations a standing sinusoidal wave, perpendicular to the reflecting surface, is established in the denser medium (FIG. 5). Although there is no net energy flow into a non adsorbing, rarer medium, there is an evanescent, nonpropagating field 3 in that medium, the electric field amplitude (E) of which is largest at the surface interface (Eo) and decays exponentially with distance (Z) from the surface according to:

$$E = E_o . \exp(-Z/d_p) \qquad 2$$

The depth of penetration ($d_p$), defined as the distance required for the electric field amplitude to fall to $\exp(-1)$ of its value at the surface, is given by:

$$d_p = \frac{\lambda/n_1}{2\eta[\sin^2\theta - (n_2/n_1)^2]^{\frac{1}{2}}} \qquad 3$$

Starting from 90°, as $\theta$ approaches $\theta_c$, $d_p$ becomes infinitely large, and at a fixed angle, increases with closer index matching (i.e., as $n_2/n_1 \rightarrow 1$). Also, because $d_p$ is proportional to wavelength, it is greater at longer wavelengths.

Thus, by an appropriate choice of the refractive index $n_1$ of the transparent waveguide, of the incident angle, and of the wavelength, one can select a $d_p$ to control optical interaction mainly with substances 4 close or at given distance from the interface and minimally with substances 5 beyond said distance. In the present embodiment, the denser medium can be constituted by the wall of the optical cell or cuvette of the invention made of plastic or glass ($n_1$ being of the order of 1.40 to 1.60) and the rarer medium is the aqueous blood sample ($n_2 = 1.34$); $\theta$ is controllably variable so that when $\lambda$ is a selected visible wavelength, $d_p$ can be varied from about 20 to 300 nm. In the unit of the invention, the materials used for the different waveguide elements, e.g. the walls of the cuvette can be different in nature, i.e. have different refractive index ($n_1$); therefore the depth of penetration of the evanescent wave component travelling in one element can be different from that in an other element, with the result that the interaction between the incident signal and the analytical species to be determined can involve regions at different depths within the solution to be analyzed.

The number of reflections (N) in the waveguide is a function of the length (L) and thickness (T) of waveguide and angle of incidence ($\theta$):

$$N = L/T . \cotg\theta \qquad 4$$

In the waveguides used here the total number of reflection for a discrete hight beam varied from about 30 to 50.

Figure 6:
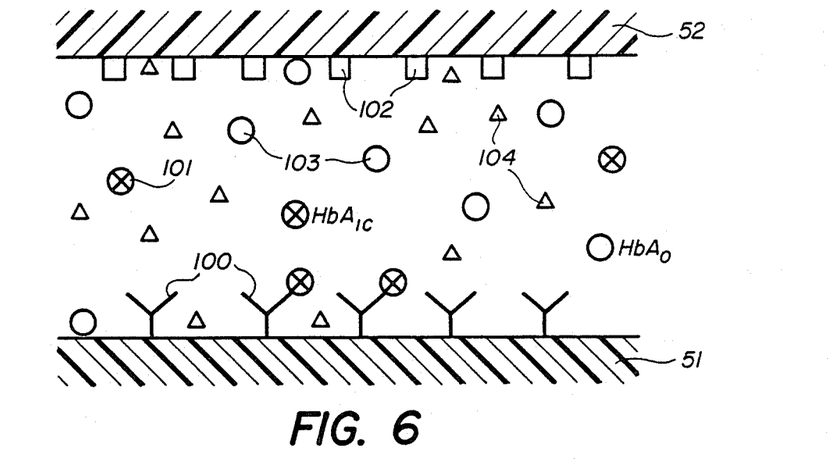
FIG. 6 is a schematized representation of the phenomena occurring during an analysis using a waveguide according to the invention.

FIG. 6 is a schematic illustration at the molecular level of the phenomena taking place during analysis in a cell of the dual-wave-guide type as disclosed previously. In FIG. 6 areas marked 51 and 52 correspond for instance to the waveguide elements 51 and 52 depicted on FIG. 1. The area intermediate between areas 51 and 52 represents schematically an analyte medium with species dissolved therein and species attached to the inside walls of elements 51 and 52. Element 51 is pictured to have deposited thereon antibodies 100 specific to $HbA_{1c}$ entities labelled 101. Some of these $HbA_{1c}$ molecules are shown after complexation with the specific antibody 100, others are still free. The other surface (i.e. the surface of element 52) is shown coated with blocking agents 102 (for instance, bovine serum albumin) said agents being intended to minimize the possible affinity of the bare wall to all Hb species in solution, for instance $HbA_o$ 103 and other proteins of any type 104.

Thus, during analysis, non-specific binding of Hb to surface 52 is prevented (or at least strongly minimized) which makes it possible, by using an angle $\theta$ of suitable value, to measure the bulk hemoglobin by the interaction of the evanescent wave component of the signal travelling in 52 with the analyte solution at depths beyond that of the blocking coating deposited on the surface.

In contrast, a complexation reaction occurs on surface 51 between the antibody molecules 100 coated thereon and the $HbA_{1c}$ (AG) molecules in the analyte solution. This reaction although rapid is not instantaneous; therefore a layer of complex progressively builds up on surface 51 with consecutive corresponding interaction with the light component travelling in that element of the waveguide, this resulting in the production of response curves of the A or B type depicted in FIG. 7 (see the examples that follow).

In order to practically carry out the tests, the glass cuvettes were cleaned by consecutive immersion in concentrated sulfuric acid and distilled water, ethanol, and acetone, using standard slide-staining glassware. Other non glass waveguides were cleaned in ethanol ultrasonically. The waveguides were contacted with the various antibody solutions. Antibodies were either physically adsorbed to the surface of the waveguides or covalently coupled. Adsorption was carried out by incubating cleaned waveguides with solutions of antibody (5 $\mu$g of protein/ml of 0.05 mol/l Tris Hcc buffer, pH 7.0) for 4 hours. Unadsorbed proteins were washed away with saline and residual protein binding sites blocked by incubation of the antibody-coated waveguides with bovine serum albumin (1.0% by weight in TRIS Buffer). The method of covalent coupling was essentially that of Weetall, involving 3-aminopropyl-triethoxysilane APTS (Immobilized Biochemicals and Affinity Chromatography, R. G. Dunlop, Plenum Press, New-York, p. 191-212) in an acid aqueous silanization environment. (Immobilized Enzymes, Antigents, Antibodies and Peptides: Preparation and Chromatography, 1: Enzymology, H. A. Weetall, Marcel Dekker Inc. New-York 1975, p. 1-48).

In general, we reacted waveguides with APTS (0.4 mol/l) for 3 hours at 80° C. We then heated the waveguides at 80°-120° C., depending on the materials involved for 2 hours, then let them soak in glutaraldehyde (0.5 mol/l) in phosphate buffer (0.1 mol/l, pH 6.8) for 90 min at ambiant temperature. The "activated" waveguides were then reacted with antiserum Ab (5 mg of protein per milliliter of phosphate buffer) for 24 hours at 4° C. After washing the antibody-coupled waveguides in phosphate buffer, we stored them at 4° C. in isotonic saline (0.14 mol/l, containing sodium azide, 8 mmol/l). Measurements of protein (Anal. Biochem 51, 654–655 (1973)) before and after the coupling demonstrated protein uptakes of approximately 1 μg/cm² on quartz.

EXAMPLE 1

Measurement of hemoglobin in the presence of foreign hemoglobin

Solution samples were prepared based on avian hemoglobin (pigeon) and containing variable proportions of human hemoglobin to be measured. The total of both hemoglobins was always 5 mg/ml in one series of samples (A) and the proportions of human hemoglobin are given in the Table below. In another series of samples (B) the total hemoglobin concentration was about doubled. A dual waveguide of the type shown in FIGS. 1 and 2 was used, one of the surfaces (e.g. 51) being coated with antibody to human IgG. The other surface (52) was blocked with bovine serum albumin as usual.

Upon doing the measurements a sharp drop (I) corresponding to transmission loss was observed in all cases; then the further drop in transmission (M) (see FIG. 7) was recorded during an interval of 10 min. In the case of the sample containing only avian hemoglobin, no further change during the 10 min interval was observed. The results are summarized below. The subscripts A and B used in FIG. 7 correspond to samples of different concentrations of total hemoglobin.

| Human Hb in avian Hb (%) | Transmission (%) (total hemoglobin) | M |
| --- | --- | --- |
| 0 | 75.3 | 0 |
| 1 | 74.9 | 0.4 |
| 2 | 74.4 | 0.9 |
| 10 | 72.0 | 3.3 |
| 20 | 68.3 | 7.0 |

Figure 7:
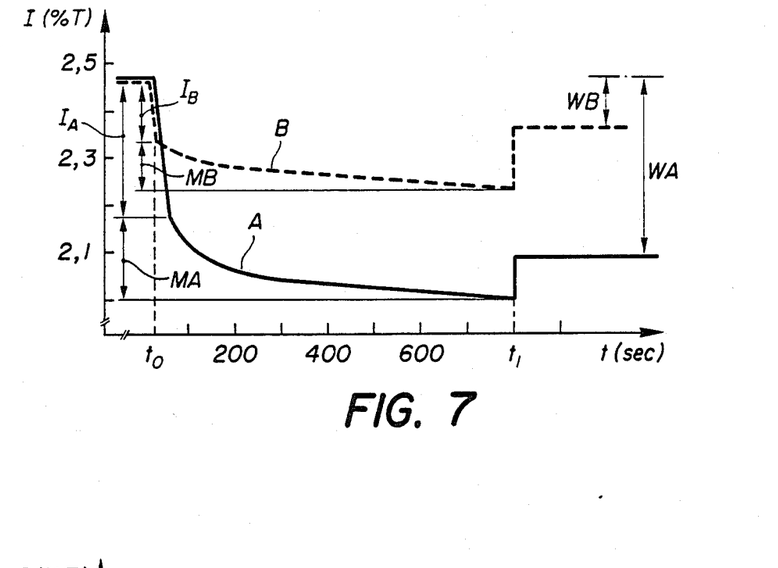
FIG. 7 is a diagram showing response curves in performing an analysis according to the aforementioned representation.

Thus the value recorded for the first initial drop I can be correlated with the total hemoglobin present while the values (M) observed after the 10 min reaction period and corresponding to the binding of the human hemoglobin factor to the antibody coated on surface 51 can be correlated with the human hemoglobin content of the sample and its ratio to total hemoglobin. Standad curves were made from the above data by recording on an automatic recorder coupled to the apparatus used in this example. Such curves were thereafter used as comparative data for determining unknown mixtures of human hemoglobin in avian hemoglobin. In FIG. 7, the values W ($W_A$ and $W_B$) correspond to the responses measured after the cell was washed thoroughly with assay buffer (at $t_1$) which removed all unbound material. The W values can also correlated, if desired, with the above analytical parameters of the solutions and used, as standards, for the analysis of unknowns.

EXAMPLE 2

Measurement of glycosylated Hemoglobin ($HbA_{1c}$) in the presence of hemoglobin Standard glycosylated Hb ($HbA_{1c}$) was prepared from pooled heparinized whole blood by cation-exchange chromatography (L. A. TRIVELLI et al., New England J. of Medicine 284 (1971), 353), using Bio-REX 70 resin (BIORAD, Richmond, Ca, USA). The purified $HbA_{1c}$ was then used to prepare standard samples by recombining it in varying known amounts with blood free from the glycosylated hemoglobin. The concentrations of $HbA_{1c}$ relative to total hemoglobin in the samples varied from 1 to 20% by weight and the total Hb concentration was of the order of 150 g/l.

Figure 8:
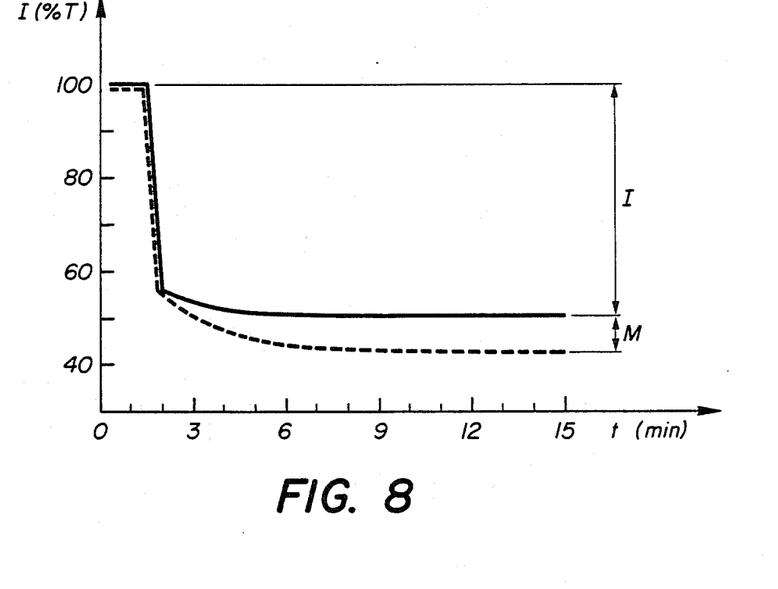
FIG. 8 is a diagram with a typical response curve in the analysis of $HbA_{1c}$, a blood component, in the presence of hemoglobin.

An analytical apparatus with cuvettes involving a dual waveguide as illustrated on FIG. 2 was used for the determinations; the inner surface of one side of the cuvette was plated with antibody specific to $HbA_{1c}$ while the surface of the opposite side was left free. The content of each cell (a fresh one was used for successively testing each standard) was about 1 ml and 0.1 ml of the standard to be measured with about 0.9 ml of PBS were pipetted therein. FIG. 8 depicts one of the titration curves obtained after 15 min incubation time (with the 20% $HbA_{1c}$ sample), the upper curve (nearly flat) being that recorded with the uncoated part of the guide and the lower curve showing the response of the antibody coated part of the waveguide.

The results of the analysis of the various standards are also gathered in the table below.

| Standard sol. under test (% $HbA_{1c}$) | (%) Transmission in waveguide | | Difference M (%) |
| --- | --- | --- | --- |
| | uncoated side | coated side | |
| 0 | 56.1 | 55.8 | 0.3 |
| 1 | 55.5 | 54.7 | 0.8 |
| 5 | 53.7 | 48.2 | 5.5 |
| 10 | 58.0 | 49.2 | 8.8 |
| 20 | 54.9 | 42.4 | 12.5 |

The difference of 0.3% for the zero $HbA_{1c}$ sample indicates some degree of residual affinity of the $HbA_{1c}$ specific antibody for the deglycosylated blood medium. This factor is however considered negligible under practical analytical conditions.

It should also be noted that the % transmission in the uncoated part of the waveguide was not constant from one cell to the other seeming to indicate that the method is not suitable for accurately determining total Hb. However it is not necessary in this instance to measure total Hb, but only to relate the signals from the uncoated and coated sides. Secondly, it is difficult to maintain a degree of constancy in manually fabricating a series of cuvettes such that each will enable full reproducibility of absolute measurements without initial calibration of the equipment. Undoubtedly, when cuvettes are manufactured industrially by molding on a large scale, this disadvantage is overcome.

We claim:

1. An immunoassay apparatus for analyzing more than one component of a single sample, the apparatus comprising:

(a) holding means for containing a liquid sample;

(b) at least two separate optical waveguide means for allowing propagation of optical signals therethrough;

(c) light source means for providing each of said waveguide means with input optical signals;

(d) detecting means for collecting output optical signals from said waveguide means and generating electrical signals representative thereof; and (e) analyzing means for receiving and processing said electrical signals from said detecting means; wherein each of said waveguide means form part of said holding means thereby exposing a surface of the waveguide means to the sample, and wherein at least one of said exposed waveguide surfaces is coated with a reactant specific to a component for which analysis is desired from said sample.

2. Apparatus of claim 1 wherein said holding means is a cuvette, and said waveguide means form opposing walls of the cuvette, the distance between said walls being from 10 to 1,000 um.

3. Apparatus as in claim 2 wherein said opposing walls are treated with different reactants specific to components which may be present in said sample, for which analysis is desired.

4. Apparatus of claim 2 wherein one of the opposing walls is treated with a reactant specific to a component which may be present in said sample and for which analysis is desired, and the other wall is treated with a blocking agent to the same component.

5. Apparatus of claim 1 wherein said light source means comprises chopper means to provide optical signals to each of said optical waveguides alternatively.

6. Apparatus of claim 5 wherein said chopper means is either a rotating mirror or a chopper disc.

7. Apparatus of claim 1 wherein said light source means comprises two independent alternately flashing light sources the output of which is focused each one optical end of said elements via a beam splitter, and in which the other end of said elements is made totally reflective so that the light signal carried by said elements travels forwards and backward therein.

8. A method of immunoassay comprising the steps of:
(a) exposing a surface of at least two separate waveguides to a liquid sample, said waveguides forming, at least in part, a container for said sample;
(b) pre-coating at least one of said waveguide surfaces with a reactant specific to a component in said sample, for which component analysis is desired;
(c) sending an optical signal through each of said waveguides, so that said optical signal impinges on the surface of said waveguide exposed to said sample as it passes through the waveguide;
(d) collecting each said optical signal; and
(e) analyzing each optical signal to determine the quantity of said component present in said sample.

* * * * *

UNITED STATES PATENT AND TRADEMARK OFFICE
CERTIFICATE OF CORRECTION

PATENT NO. : 4,775,637
DATED : October 4, 1988
INVENTOR(S) : Ranald M. Sutherland, et al It is certified that error appears in the above-identified patent and that said Letters Patent is hereby corrected as shown below:

IN THE HEADING:

At section [73] Assignee:, please change the spelling of the assignee's name to read:

--PRUTEC LIMITED--.

Signed and Sealed this

Eleventh Day of April, 1989

*Attest:*

DONALD J. QUIGG

*Attesting Officer*     *Commissioner of Patents and Trademarks*